United States Patent [19]

Borjas et al.

[11] Patent Number: 5,567,299

[45] Date of Patent: *Oct. 22, 1996

[54] PROCESS FOR THE ELECTROCHEMICAL OXIDATION OF ARYLKETONES

[75] Inventors: Ricardo E. Borjas, Corpus Christi, Tex.; Carina Araullo-McAdams, Wilmington, N.C.; Steven R. Alexander; George A. Blay, both of Corpus Christi, Tex.; Yaw-Hwa Liu, Sugarland, Tex.

[73] Assignee: Hoechst Celanese Corporation, Somerville, N.J

[ * ] Notice: The term of this patent shall not extend beyond the expiration date of Pat. No. 5,500,099.

[21] Appl. No.: 577,679

[22] Filed: Dec. 21, 1995

Related U.S. Application Data

[63] Continuation of Ser. No. 437,595, May 9, 1995, Pat. No. 5,500,099.

[51] Int. Cl.$^6$ ..................................................... C25B 3/02

[52] U.S. Cl. ............................................................. 205/449
[58] Field of Search ............................................... 205/449

[56] References Cited

U.S. PATENT DOCUMENTS 5,500,099   3/1996   Borjas et al. .......................... 205/449

*Primary Examiner*—Bruce F. Bell
*Assistant Examiner*—Kishor Mayekar
*Attorney, Agent, or Firm*—James J. Mullen; Donald R. Cassady

[57] ABSTRACT

The present invention provides a process for preparing arylglyoxals which comprise the steps of (a) electrochemically oxidizing an arylketone at a pH of less than about seven and at a temperature of from about −20° C. to about 120° C. in the presence of an electrolyte for a sufficient period of time to form an arylacetal, and (b) subjecting said acetal to hydrolysis for a sufficient period of time and under suitable temperature and pressure conditions to form said arylglyoxal.

22 Claims, No Drawings

PROCESS FOR THE ELECTROCHEMICAL OXIDATION OF ARYLKETONES

This is a continuation of application Ser. No. 08/437,595 filed on May 9, 1995, now U.S. Pat. No. 5,500,099.

BACKGROUND OF THE INVENTION

1. Field of the Invention

The present invention relates to arylglyoxals (such as substituted and unsubstituted phenylglyoxals) and, more particularly, to a method for the preparation thereof. Still more particularly, the present invention discloses methods for preparing arylglyoxals (such as substituted and unsubstituted phenylglyoxals) from corresponding arylketones (such as substituted and unsubstituted acetophenones).

2. Description of the Prior Art

The following prior art references are disclosed in accordance with the terms of 37 CFR 1.56, 1.97, and 1.93.

Substituted phenylglyoxals such as hydroxyphenylglyoxal (hereinafter referred to sometimes as "HPGO") are well-known compounds that are useful in the production of intermediate products which are utilized for the preparation of pharmaceutical products. In *Organic Syntheses*, Coll Vol. 2, A. Blatt, edd., (1943) at p. 509, a method is disclosed for the production of unsubstituted phenylglyoxals from an acetophenone. That method uses the toxic substances selenium dioxide ($SeO_2$) thereby posing undesirable health hazards and disposal problems.

D. T. Manning and H. A. Stansbury, Jr., *J. Am. Chem. Soc.*, 81, 4885–90 (1959) discloses the reaction of an unsubstituted acetophenone with nitrosyl chloride in ethanol to give a 12.4 percent yield of phenylglyoxal diethyl acetal. In addition, other reaction products are generated in that reaction.

U.S. Pat. No. 4,013,680 discloses a two-step method for the preparation of α-keto acids such as phenylglyoxylic acid by the oxidation of methyl ketones in aqueous solution with an inorganic nitrite salt and hydrochloric or sulfuric acid. It suggests that the reaction proceeds via the formation of a glyoxal intermediate.

U.S. Pat. No. 4,272,453 discloses a method for the preparation of 1-chloro-1-p-methoxybenzoylformaldoxime by the addition of p-methoxyacetophenone to nitrosyl chloride in carbon tetrachloride.

U.S. Pat. No. 3,794,620 discloses the reaction of nitrosyl chloride with aromatic acetyl derivatives. According to that patent, three moles of nitrosyl chloride are required for each acetal group.

German Patent DE 2,432,563 discloses the oxidation of substituted acetophenones using alkyl nitrites in alcohol and hydrochloric acid to prepare substituted phenylglyoxalacetals.

German Patent DE 3,539,629 discloses a method of oxidizing substituted acetophenones using dinitrogen trioxide in alcohol/hydrochloric acid to prepare appropriate substituted phenylglyoxal acetals.

U.S. Pat. No. 5,124,489 discloses the reaction of a substituted acetophenone with a primary or a secondary alcohol in the presence of a source of a hydrogen ion ($H^+$) and a source of a nitrosonium ion ($NO^+$) to form a corresponding substituted phenylglyoxalacetal. That patent however, does not disclose the formation of the substituted phenylglyoxal.

The present invention discloses an improved method for the preparation of arylglyoxals such as a substituted or an unsubstituted phenylglyoxal from a corresponding arylketone such as a substituted or unsubstituted acetophenone. The method involves fewer steps for the addition of reactants, avoids the use of toxic materials and complicated extraction procedures, and provides for the reaction to be carried out in one reactor.

These and other advantages and objects of the present invention will become apparent from the following description.

All of the above-cited prior art and any other references mentioned herein are incorporated herein by reference in their entirety.

SUMMARY OF THE INVENTION

There is provided in the present invention an efficient and novel process for preparing arylglyoxals which comprises the steps of (a) electrochemically oxidizing an arylketone at a pH of less than about seven and at a temperature of from about −20° C. to about 120° C. in the presence of an electrolyte for a sufficient period of time to form an arylacetal, and (b) subjecting said acetal to hydrolysis for a sufficient period of time and under suitable temperature and pressure conditions to form said arylglyoxal.

DETAILED DESCRIPTION OF THE INVENTION

The present invention provides a novel process in the electrochemical area and which process overcomes significant prior art problems. Thus, there is provided a process for preparing arylglyoxals which comprises the steps of (a) electrochemically oxidizing an arylketone at a pH of less than about seven and at a temperature of from about −20° C. to about 120° C. in the presence of an electrolyte for a sufficient period of time to form an arylacetal, and (b) subjecting said acetal to hydrolysis for a sufficient period of time and under suitable temperature and pressure conditions to form said arylglyoxal.

The starting materials are arylketones having the general formula:

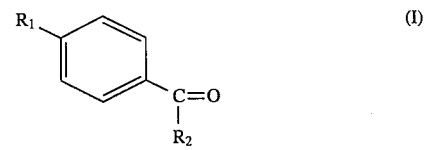

wherein $R_1$ is hydrogen, hydroxy, alkyl ($C_1$–$C_8$), carboxylate

where R is $C_1$–$C_8$), and esters; and $R_2$ is $C_1$–$C_8$.

The arylglyoxals produced by the novel process of the present invention have the general formula:

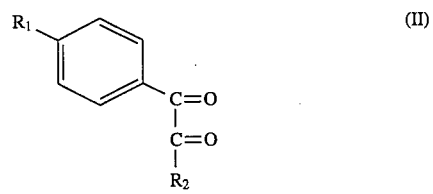

wherein $R_1$ and $R_2$ have the same values as set forth in Formula I.

In the present process, a wide variety of arylketones can be convened to the corresponding arylacetals and then hydrolyzed to the corresponding arylglyoxals. An example of the present invention process is shown in Scheme 1.

SCHEME 1

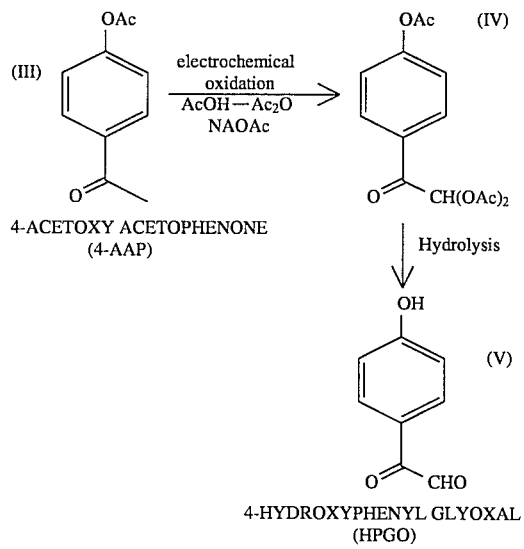

4-ACETOXY ACETOPHENONE
(4-AAP)

4-HYDROXYPHENYL GLYOXAL
(HPGO)

The present process is capable of achieving good yields of arylacetals (and subsequently arylglyoxals) with yields generally better than 50% and often up to 80 or 90% or higher, based on arylketone reacted.

In step (a), the electrolytic reaction (sometimes referred to as anodic oxidation) of the present invention can be effected under usual conditions for effecting reactions of organic compounds at the anode. The electrolysis is carded out by passing an electric current through a solution of the arylketone. Procedures for effecting electrochemical reactions of organic compounds are well-documented in the literature and such procedures can be employed in the present process. In particular, procedures for effecting electrochemical reactions in non-aqueous solvents are generally suitable and can be used (see those described in Experimental Electrochemistry for Chemists, Sawyer & Roberts, John Wiley & Sons, 1974), with particular reference to Chapter 4, Solvents & Electrolytes, and the non-aqueous solvents at pages 203–210. In order to obtain good solubility of the arylketone reactant, it is desirable to use an organic solvent. As most organic solvents have poor conductivity, the use of electrolytes is indicated, generally referred to as supporting electrolytes. As supporting electrolyte, it is generally preferred to employ those which will not undergo an interfering discharge under the electrolysis conditions. In the present invention, this primarily concerns discharge at the anode as the desired reaction occurs at the anode, and suitable electrolytes are described in the above referred-to Sawyer & Roberts text. In particular, electrolytes that are found suitable are NaOAc; $NH_4OAc$; $(R)_4NClO_4$, $(R)_4NBF_4$, $(R)_4NOTs$—where R is Me, Et, Pr, or Bu; NaOAc—$(R)_4NClO_4$; $(R)_3N$; $LiClO_4$; $KClO_4$; $NaClO_4$; $KNO_3$; $KBF_4$; $K_2S_2O_8$; LiCl; $(Me)_4NCl$; $(Bu)_4NBr$; NaBr; $NaBI_4$, KF, and mixtures thereof.

In the present process, water or moisture is generally deleterious. It has been found that the presence of water contributes to undesirable side reactions, with one of the products apparently being a dimer derivative of the starting arylketone reactant. The present process is appropriately conducted in non-aqueous solvents, and particularly in those classed as polar or dipolar aprotic and protic solvents as described on page 203 of the above referred to Sawyer & Roberts text, particularly including acetonitrile, dimethylformamide, dimethyl sulfoxide, hydrogen fluoride (liquid), ammonia (liquid), fluorosulphuric acid, methanol, formic acid, acetic acid, trifluoroacetic acid, dimethylacetamide, hexamethylphosphor-triamide, AcOH/tert BuOH, MeOH, and mixtures thereof.

The present electrolytic reaction can be conducted in the various types of electrolysis cells known to the art. In general, such cells comprise a container made of material capable of resisting action of electrolytes, e.g. glass or plastics, and a cathode and anode which are electrically connected to a source of electric current.

The materials which are used for the anode and cathode are independently selected from the group consisting of carbon, platinum, Ru, Rh, Pd, Os, iridium, lead dioxide, magnetite, stainless steel, silver, nickel, lead, copper, gold, graphite, mercury, iron, tin, copper, and aluminum; see Organic Electro-Chemistry, edited by Baizer & Lund, Second Edition (1983), Marcel Dekker, Inc., NY, N.Y., page 182.

In the present invention process, as in other electrolytic reactions, there is a possibility of interference between reactions at the cathode and anode. Thus, if a halide electrolyte is used, e.g. a bromide, bromine can be produced at the anode and if the bromine migrates to the cathode, it can be reduced, thereby lowering current efficiency. If an unsaturated compound is provided to take up the bromine, it or the resulting bromide, can react with cathode reduction products, thereby interfering with desired reactions. It is possible to conduct the desired oxidation in an undivided cell, and some of the adverse effects can be lessened by selection of suitable salts or other material for an anode oxidation. Thus, for example, an oxalate salt can be used, in a manner similar to that found successful in an undivided cell using a quarternary ammonium oxalate electrolyte; see Angew, Chem. Int. Ed. Engl. 22, 492 (1983); Angew Chem. Suppl. 1983, 691–702; European patent application no. 0028430, Oct. 20, 1980. Good results can also be obtained if a divided cell is employed with a separator to prevent the free flow of components between the cathode and anode. A mechanical barrier can be used which has some permeability, e.g., a fritted glass filter, glass cloth, asbestos, porous vinyl chloride, etc. It is generally better to employ a selective membrane, such as an ion exchange membrane, particularly permselective cation exchange membranes which selectively permit migration of cations. Such membranes as described in U.S. Pat. No. 3,193,480 can suitably be employed. Suitable membranes are often characterized by having sulfonyl groups on a relatively impermeable polymeric material which is inert to and resistant to degradation by the electrolysis medium.

The electrolysis cells used in the examples herein are suitable for the present process, although the H-cell utilized in many of the examples is generally more appropriate for laboratory procedures than for large scale production. For large scale operations, it is likely that a flow cell would be used, similar to that in some of the illustrative examples, with a narrow gap between electrodes separated by a membrane divider, and separate catholyte and anolyte streams flowing past their respective electrodes. Further description of suitable cells can be found in the above-referenced Organic Electrochemistry, noting particularly chapter 5 on Practical problems in Electrolysis, and chapter 30 on Industrial Electroorganic Chemistry which describes several commercially used electrolysis cells. When a divided cell is used, it is possible to employ the same electrolysis medium on both the cathode or anode sides, or to employ different media.

In the present process, the reactants and electrolytes can be used over broad concentration ranges as found convenient. Electrolyte salts will generally be provided in amounts for acceptable conductivity and solubility, in amounts, for example, from about 0.02 molar up to about 0.5 molar, or the limit of solubility. Similarly, the arylketone can be used in amounts as low as convenient for efficient handling up to the solubility limit, or, for example, from about 0.02 molar up to about 0.4 molar or so. If desired, the solubility limits can be exceeded for the salts or the arylketone reactant, but it will generally be convenient to utilize an essentially single phase reaction medium.

In effecting the electrolysis, current is applied to the cell and the proper cathode voltage is obtained due to the discharge characteristics of the arylketone in the reaction system. If desired, the discharge voltage can also be regulated by appropriate electrical means, but that is not necessary. The electrolysis can be conducted at usual current densities for such procedures, with ranges from about 25 to 150 or so milliamperes per square centimeter ($mA/cm^2$) being convenient in laboratory procedures. In general, for efficient use of current, the current density will be chosen so as not to exceed the mass transfer rate of the component to be oxidized at the electrode. In large scale operations, the appropriate current density can be selected in accordance with overall economics of the production process, as discussed in chapter 30 of the above-referenced Organic Electrochemistry, possibly using currents in the 10–100 amperes per square decimeter range described there. The text is of further interest for its discussion of electrolytes and solvents for electrolysis, e.g. at page 205, noting that for reductions, dimethylformamide has a usable potential range comparable to acetonitrile. Additional useful information on electrolysis conditions can be found in U.S. Pat. No. 4,404,069 and U.S. Pat. No. 4,356,317. The teaching of these patents, along with that of Organic Electrochemistry, Experimental Electrochemistry for Chemists, U.S. Pat. No. 4,028,201 and U.S. Pat. No. 3,193,480, all referenced hereinabove, is incorporated by reference; attention is particularly directed to aspects concerning electrolysis in non-aqueous, aprotic solvent systems.

The present process can be effected at ambient temperatures, or at higher or lower temperatures, e.g. from about −20° C. to about 120° C. or higher, as found convenient. Use of low temperatures in this type of reaction may have a moderate influence in improving results, but this is offset by the potential added costs in employing refrigeration means to achieve low temperatures. Some cooling means may be indicated to offset the heat generated by electric current, such as cooling sufficient to maintain near ambient conditions.

The process according to the invention in step (a) may be carried out batchwise, semi-continuously, or fully continuously. In the first case, the whole quantity of arylketone is introduced, quantities greater than those capable of being dissolved in the electrolyte being likewise possibly used. In the semi-continuous method, the same amount is added gradually, in the same measure as it is consumed during electrolysis. The total of the quantities used, for example, are in the range of from approximately one to fifty parts by weight, preferably from about five to 23 parts by weight per 100 parts by weight of the electrolyte. The continuous process is performed by connecting several electrolysis cells in cascade form. For improving the current efficiency, the charge preferably is not completely electrolyzed, but electrolysis is stopped when a conversion of about 90%, preferably, of about 80% is reached.

The reaction mixture is worked up in the usual manner, for example, by distilling off the solvent and the starting material which has not reacted and by subsequently distilling the crude product under an adequately reduced pressure or by extraction and/or crystallization of the products of the process of the invention, step (a).

When using quarternary ammonium or phosphonium compounds as conducting salts, the work-up can be performed according to the following method: The reaction mixture is extracted, preferably after concentration, which may also be performed in-vacuo, with approximately three to five times the quantity by volume of a suitable solvent, for example, petroleum ether, for example, in a pulsation column, distilled off after having separated the extracting agent and the residue is distilled by fractionation. The arylacetal crystallizes from the distillate and may be further purified by recrystallization, for example, from hexane and cyclohexane.

The products of the process of the invention, step (a), may be converted into the corresponding arylglyoxals in known manner by acidic hydrolysis. Such hydrolysis takes place at a temperature greater than the freezing point of water, preferably from about 5° C. to about 100° C., more preferably from about 15° C. to about 90° C. The pressure during such hydrolysis is not critical and may be sub-atmospheric, atmospheric, or super-atmospheric. The time also is not critical as long as the desired end product (glyoxal) is obtained. This may require at least one minute to twelve hours or longer.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

In a double-walled H cell cooled with water, having a volume of about 750 ml, 20 g of 4-acetoxyacetophenone (4-AAP) is dissolved in an electrolyte consisting of 650 ml of methanol, 75 ml of glacial acetic acid, and 7.5 g of KF are electrolyzed at a cylindrical platinum wire-gauze electrode ($\phi$4 cm, height 4 cm) as anode and a tube of Cr—Ni steel of a diameter of 12 mm as cathode which is separated from the anode by a porous polyethylene tissue, with a constant current intensity of about 0.1 amperes to about 3.5 amperes at a temperature of 22° C. until 18.5 Ah is passed. Stirring is effected by means of a magnetic rod agitator fixed at the bottom of the cell.

Methanol as well as 4-AAP are used in a technically pure quality. For working up, methanol and 4-AAP are distilled off and 8 g of 4-acetoxyacetophenone acetal (having a melting point of 48° C.) is distilled from the crude product obtained (16 g) at a temperature of from 86° C. to 89° C. and under a pressure of 0.3 mm Hg, which corresponds to a yield of substance of 81% of the theory.

The iodometrical determination according to the reaction equation (as shown in Scheme 1) reveals a current efficiency of 36.8% which corresponds to a yield of substance of 86% of the theory. The crude acetal product is then subjected to hydrolysis for a period of two hours at a temperature of 60° C. to form the 4-hydroxyphenyl glyoxal (HPGO).

EXAMPLE 2

Example 1 above is repeated, except that during electrolysis, a constant voltage of from 5 to 20 volts is maintained. The results are essentially the same, except that the end product yields are improved by about 10%.

EXAMPLE 3

Under the same conditions as in Example 1, 20 g of 4-ethoxyacetophenone are electrolyzed at two graphite plates (Diabon®) of 4×10×0.5 cm fixed at a distance of 0.8 cm from each other with a current intensity of 2.2 amperes until 18.5 Ah is delivered. The iodometrical determination revealed a current efficiency of 31.5% for acetal. This acetal is then hydrolyzed under the conditions of Example 1 and the end product is 4-ethoxybenzyl glyoxal.

EXAMPLE 4

Under the same conditions as in Example 1, 35 g of 4-methyl acetophenone is electrolyzed until 11 Ah is passed. The iodometrical titration indicated a current efficiency of 37% for the formation of the corresponding acetal. Upon hydrolysis, the end product is 4-methyl benzyl glyoxal.

EXAMPLE 5

In a standard undivided cell having a platinum anode and a glossy carbon cathode (33 cm² each) there is charged 200 g methanol (65° C.), 11.3 g of 4-methoxyacetophenone (4-MAP), and 11.5 g tetraethylammonium toluene sulfonate. This electrolysis is conducted at a current density of about 30 mA/cm² until a current passage of 50.9 Ah is charged (633% of theoretical value). According to an iodometrical determination, a current efficiency of 50% is obtained. About 150 g methanol is distilled off and the remaining solution is neutralized with aqueous NaHCO₃ and extracted with ethyl acetate. The extract is dried and the solvent is removed by evaporation. The remaining oil is separated by column chromatography (silica gel, MTBE/cyclohexane= ¼). The acetal product is 6.4 g of 2,2-dimethoxy-1-[4'-methoxyphenyl]-ethanale (41% based on 4-MAP). Subsequent hydrolysis at 62° C. yields 4-hydroxyphenyl glyoxal (HPGO).

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing arylglyoxals which comprises the steps of (a) electrochemically oxidizing an arylketone at a pH of less than about seven and at a temperature of from about −20° C. to about 120° C. in the presence of an electrolyte for a sufficient period of time to form an arylacetal, and (b) subjecting said acehal to hydrolysis for a sufficient period of time and under temperature and pressure conditions to form said arylglyoxal.

2. The process as set forth in claim 1 wherein in step (a), the temperature is from about 0° C. to about 100° C.

3. The process as set forth in claim 1 wherein in step (a), there is also included a solvent.

4. The process as set forth in claim 1 wherein in step (a) the electrochemical oxidation is conducted in an undivided cell.

5. The process as set forth in claim 1 wherein in step (a) the electrochemical oxidation is conducted in a divided cell.

6. The process as set forth in claim 3 wherein the temperature in step (a) is from about 0° C. to about 100° C.

7. The process as set forth in claim 4 wherein in step (a) there are two electrodes in said cell and which are independently made of a material selected from the group consisting of carbon, platinum, iridium, lead dioxide, magnetite, stainless steel, silver, nickel, lead, copper, gold, and graphite.

8. A process for preparing 4-hydroxyphenyl glyoxal which comprises the steps of (a) electrochemically oxidizing a 4-acetoxyacetophenone at a pH of less than about seven and at a temperature of from about −20° C. to about 120° C. in the presence of an electrolyte for a sufficient period of time to form the corresponding acetal, and (b) subjecting said acetal to hydrolysis for a sufficient period of time and under temperature and pressure conditions to form said glyoxal.

9. The process as set forth in claim 8 wherein in step (a), the temperature is from about 0° C. to about 100° C.

10. The process as set forth in claim 8 wherein in step (a), there is also included a solvent.

11. The process as set forth in claim 8 wherein in step (a), the electrochemical oxidation is conducted in an undivided cell.

12. The process as set forth in claim 8 wherein in step (a), the electrochemical oxidation is conducted in a divided cell.

13. The process as set forth in claim 10 wherein the temperature in step (a) is from about 0° C. to about 100° C.

14. The process as set forth in claim 11 wherein in step (a), there are two electrodes which are independently made of a material selected from the group consisting of carbon, platinum, iridium, lead dioxide, magnetite, stainless steel, silver, nickel, lead, copper, gold, and graphite.

15. A process for preparing arylacetals which comprises the step of electrochemically oxidizing an arylketone at a pH of less than about seven and at a temperature of from about −20° C. to about 120° C. in the presence of an electrolyte for a sufficient period of time to form said arylacetals.

16. The process as set forth in claim 15 wherein the temperature is from about 0° C. to about 100° C.

17. The process as set forth in claim 15 wherein there is also included a solvent.

18. The process as set forth in claim 15 wherein the electrochemical oxidation is conducted in an undivided cell.

19. The process as set forth in claim 15 wherein the electrochemical oxidation is conducted in a divided cell.

20. The process as set forth in claim 17 wherein the temperature is from about 0° C. to about 100° C.

21. The process as set forth in claim 18 wherein there are two electrodes in said cell and which are independently made of a material selected from the group consisting of carbon, platinum, iridium, lead dioxide, magnetite, stainless steel, silver, nickel, lead, copper, gold, and graphite.

22. The process as set forth in claim 16 wherein the temperature is from about 20° C. to about 50° C.

* * * * *